United States Patent
Hu et al.

(10) Patent No.: US 11,993,786 B2
(45) Date of Patent: May 28, 2024

(54) METHODS AND COMPOSITIONS FOR GENERATING PACEMAKER CELLS

(71) Applicant: Yu-Feng Hu, Taipei (TW)

(72) Inventors: Yu-Feng Hu, Taipei (TW); Tze-Wen Chung, Hsinchu (TW); Shih-Ann Chen, Taipei (TW)

(73) Assignees: TAIPEI VETERANS GENERAL HOSPITAL, Taipei (TW); NATIONAL YANG MING CHIAO TUNG UNIVERSITY, Hsinchu (TW)

( * ) Notice: Subject to any disclaimer, the term of this patent is extended or adjusted under 35 U.S.C. 154(b) by 1259 days.

(21) Appl. No.: 15/798,619

(22) Filed: Oct. 31, 2017

(65) Prior Publication Data

US 2019/0127689 A1  May 2, 2019

(51) Int. Cl.
| | |
|---|---|
| *A61K 35/34* | (2015.01) |
| *A61N 1/32* | (2006.01) |
| *C12N 5/0735* | (2010.01) |
| *C12N 5/077* | (2010.01) |
| *A61N 1/37* | (2006.01) |
| *C12N 5/071* | (2010.01) |
| *C12N 5/074* | (2010.01) |

(52) U.S. Cl.
CPC .......... *C12N 5/0606* (2013.01); *A61N 1/326* (2013.01); *C12N 5/0657* (2013.01); *A61K 35/34* (2013.01); *A61N 1/3702* (2013.01); *C12N 5/0692* (2013.01); *C12N 5/0696* (2013.01); *C12N 2500/82* (2013.01); *C12N 2501/10* (2013.01); *C12N 2506/02* (2013.01); *C12N 2510/00* (2013.01); *C12N 2510/02* (2013.01); *C12N 2533/52* (2013.01)

(58) Field of Classification Search
CPC ...... A61K 35/34; A61N 1/326; A61N 1/3702; C12N 5/0606; C12N 5/0657; C12N 5/0692; C12N 5/0696; C12N 2500/82; C12N 2501/10; C12N 2506/02; C12N 2510/00; C12N 2510/02; C12N 2533/52
See application file for complete search history.

(56) References Cited

FOREIGN PATENT DOCUMENTS

WO  WO-2015071912 A1 *  5/2015

OTHER PUBLICATIONS

Sionkowska et al., "Preparation and characterization of silk fibroin/chitosan composite sponges for tissue engineering", 2013, Journal of Molecular Liquids 178, p. 5-14.*
Cheerarot et al., "Biodegradable silk fibroin/chitosan blend microparticles prepared by emulsificationdiffusion method", 2015, e-Polymers 15(2), p. 67-74.*
Patra et al., "Silk protein fibroin from Antheraea mylitta for cardiac tissue engineering", 2012, Biomaterials 33, p. 2673-2680.*
Chi et al., "Cardiac repair using chitosan-hyaluronan/silk fibroin patches in a rat heart model with myocardial infarction", epub 2012, Carbohydrate Polymers 92, p. 591-597.*
Gorenek et al., "Cardiac arrhythmias in acute coronary syndromes: position paper from the joint EHRA, ACCA, and EAPCI task force", 2014, EP Europace 16(11), p. 1655-1673.*
Kundu et al., "Silk fibroin biomaterials for tissue regenerations", epub 2012, Advanced Drug Delivery Reviews 65, p. 457-470.*

* cited by examiner

*Primary Examiner* — Michael D Burkhart
(74) *Attorney, Agent, or Firm* — NZ Carr Law Office PLLC

(57) ABSTRACT

Disclosed herein are methods and compositions for generating pacemaker cells from non-pacemaker cardiomyocytes. For example, the method includes the step of culturing the non-pacemaker cardiomyocytes with silk fibroin so that the silk fibroin induces the transformation of at least a portion thereof into pacemaker cells.

3 Claims, 14 Drawing Sheets
(4 of 14 Drawing Sheet(s) Filed in Color)

METHODS AND COMPOSITIONS FOR GENERATING PACEMAKER CELLS

BACKGROUND OF THE INVENTION

1. Field of the Invention

The present disclosure relates to methods and compositions for generating the biological pacemakers; more particularly, to methods and compositions that use silk fibroins for generating the biological pacemakers.

2. Description of Related Art

The term "cardiac arrhythmia" encompasses a group of medical conditions in which the heartbeat is too fast, too slow, or irregular. The symptoms of cardiac arrhythmia range from barely perceptible to cardiovascular collapse and death.

Cardiac arrhythmias are due to problems with the electrical conduction system of the heart. The cardiac conduction system comprises a group of specialized cardiac muscle cells that send electrical signals to the heart muscle and thereby cause it to contract. The main components of the cardiac conduction system are the sinoatrial node (SAN), atrioventricular (AV) node, bundle of His, and Purkinje fibers. During cardiogenesis, cardiomyocytes become specialized to exhibit either ventricular, atrial, or pacemaker properties. The SAN, the primary pacemaker region of the heart, is a highly-specialized structure containing approximately 10,000 to 15,000 pacemaker cells or less. These pacemaker cells in the SAN generate an electrical impulse that originates from the right atrium of the heart, in particular, the SAN. This impulse then passes through the AV node and through both ventricles via the Bundle of His and the Purkinje fibers. The result is a synchronized contraction of the heart muscle, and thus, blood flow.

Normal heart rates range from 50 to 100 beats per minute in an adult at rest. The term bradyarrhythmias refers to a heart rate slower than the normal heart rate (i.e., fewer than 50 times per minute). Bradyarrhythmias occur when electrical signals from the cardiac conduction system slow down or are blocked; common causes of bradyarrhythmias include sinus bradycardia (slow electrical impulses from the sinus node), sinus arrest (pauses in the normal activity of the sinus node), and AV block (blockages of the electrical impulse from the atria to the ventricles). Bradycardia may lead to low cardiac output and oxygen-rich blood in the body, which is associated with exercise intolerance, syncope, and sudden cardiac death.

Current therapies for cardiac bradyarrhythmias rely on an implanted electronic pacemaker that helps the heart maintain an appropriate rate. However, the electronic pacemakers are quite expensive, and the implantation of such electronic devices may lead to various complications, including pulmonary collapse, hemorrhage, bacterial infection, as well as device malfunctions (e.g., lead/generator failure). These drawbacks limit the applicability of this technique. Therefore, the related art seeks eagerly for alternative treatment options of bradyarrhythmias.

Several investigational therapies, including cell therapies and gene therapies, have been reported to create biological pacemakers which produce specific electrical stimuli that mimic that of the body's natural pacemaker cells. In the cell therapy, stem cells (including induced pluripotent stem cells or embryonic stem cells) are converted into pacemaker cells. In gene therapy, the biological pacemakers are made by the expression of genes that increase excitability or diastolic depolarization, or that specify a sinus-node phenotype. Yet the clinical application of these technologies remains obscure. To begin with, the administration of foreign cells during the cell therapy often trigger the immune response of the recipient. Further, there is no standardized way to manufacture and validate the cell products to be used. Also, the beating rates from implanted cardiomyocytes or transgenic stem cell are too slow to fit the needs until now. On the other hand, gene therapy involving, for example, TBX18 gene, could create a satisfactory beating rate. The effect, however, seems short-term. However, the use of viral vectors for the gene therapy might induce the cardiac immune response. Additionally, the manufacture and validation of the viral product are also difficult to standardize. Vectors containing other genes, including TBX3, hyperpolarization-activated cyclic nucleotide-gated (HCN) channels, beta-2 receptors, adenylyl cyclase, SKM1 are facing similar problems.

In view of the foregoing, there exists a need in the related art for providing a method and composition for generating pacemaker cells so as to address the disadvantages faced by conventional art.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

Considering the facts discussed above, one purpose of the present invention is to provide a novel strategy to generate cells with pacemaker activity; in some embodiments, cells with induced pacemaker activity are similar to those in the SAN. Moreover, the proposed preparation method is easily standardizable. Therefore, in one aspect, the present disclosure is directed to a method for generating pacemaker cells (e.g., SAN-like cells) from non-pacemaker cardiomyocytes.

According to some embodiments, the method comprises the step of contacting a cell population comprising non-pacemaker cardiomyocytes with an effective amount of a silk fibroin biomaterial so that the one or more of the cells are transformed into the pacemaker cells.

In some optional embodiments, the cell population and the silk fibroin biomaterial are contacted in vitro. In these cases, the method further comprises the step of culturing the cell population with the silk fibroin biomaterial under a suitable condition so that one or more of the non-pacemaker cardiomyocytes are transformed into the pacemaker cells.

In other optional embodiments, the cell population and the silk fibroin biomaterial are contacted in vivo so that at least a portion of the non-pacemaker cardiomyocytes are transformed into the pacemaker cells in situ.

According to various embodiments of the present disclosure, the silk fibroin biomaterial is a silk fibroin solution, a silk fibroin particle, a non-woven silk fibroin mat, a silk fibroin hydrogel, a silk fibroin film, or a silk fibroin scaffold. For example, the silk fibroin film comprises a biodegradable polymeric film having a plurality of amines group on the surface thereof, and a plurality of silk fibroins crosslinked with the biodegradable polymeric film via the plurality of amine groups.

In another aspect, the present invention is directed to pacemaker cells. According to various embodiments of the present disclosure, the pacemaker cells are generated using the in vitro method according to the above-mentioned aspect/embodiments of the present disclosure. For example, the method comprises the step of, culturing a cell population comprising non-pacemaker cardiomyocytes with an effective amount of a silk fibroin biomaterial so that the one or more of the non-pacemaker cardiomyocytes are transformed into the pacemaker cells.

According to optional embodiments of the present invention, the pacemaker cells comprise SAN-like cells. Still optionally, the SAN-like cells exhibit an increased expression level of hyperpolarization-activated, cyclic nucleotide-gated potassium channel 4 (HCN4) gene or connexin 45 gene, or both, compared with the cells that are not transformed. Still optionally, the SAN-like cells exhibit sinoatrial node-specific calcium clock.

In yet another aspect, the present disclosure is directed to a pharmaceutical composition for treating cardiac arrhythmia.

According to some embodiments, the pharmaceutical composition comprises an effective number of pacemaker cells according to the above-mentioned aspect/embodiments and a pharmaceutically acceptable carrier thereof.

In optional embodiments, the pharmaceutical composition further comprises an effective amount of a silk fibroin biomaterial. For example, the silk fibroin biomaterial may be in the form of a silk fibroin solution, a silk fibroin particle, a non-woven silk fibroin mat, a silk fibroin hydrogel, a silk fibroin film, or a silk fibroin scaffold.

In still another aspect, the present disclosure is directed to a method for treating a subject suffering from cardiac arrhythmia.

According to certain embodiments, the treatment method comprises the step of administering to the subject an effective number of pacemaker cells or a pharmaceutical composition according to any of the above-mentioned aspects/embodiments of the present invention.

In some optional embodiments, the cell population used to prepare the pacemaker cells is derived from the subject.

According to some other embodiments, the treatment method involves the in-situ formation of pacemaker cells. In these cases, the method comprises the step of administering to the heart of the subject an effective amount of a silk fibroin biomaterial.

According to various embodiments of the present disclosure, the silk fibroin biomaterial is a silk fibroin solution, a silk fibroin particle, a non-woven silk fibroin mat, a silk fibroin hydrogel, a silk fibroin film, or a silk fibroin scaffold. For example, the silk fibroin film comprises a biodegradable polymeric film having a plurality of amines group on the surface thereof, and a plurality of silk fibroins crosslinked with the biodegradable polymeric film via the plurality of amine groups.

Subject matters that are also included in other aspects of the present disclosure include the use of a silk fibroin biomaterial in the manufacture of a medicament for use in the treatment of cardiac arrhythmia or in the generation of pacemaker cells, as well as a silk fibroin biomaterial for use in the treatment of cardiac arrhythmia or in the generation of pacemaker cells. For example, the silk fibroin biomaterial may be in the form of a silk fibroin solution, a silk fibroin particle, a non-woven silk fibroin mat, a silk fibroin hydrogel, a silk fibroin film, or a silk fibroin scaffold.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

The patent or application file contains at least one drawing executed in color. Copies of this patent or patent application publication with color drawing(s) will be provided by the Office upon request and payment of the necessary fee.

DESCRIPTION

Figure 1A:
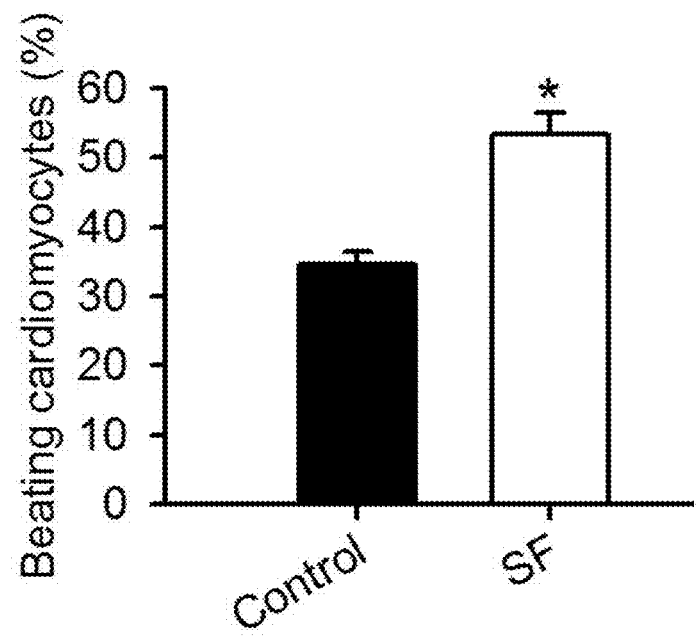
FIG. 1A and FIG. 1B are bar graphs respectively illustrating the incidence of beating cardiomyocytes and the beating rate (beat per minute) in cardiomyocytes, according to one working example of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

According to the present disclosure, the term "pacemaker cells" refers to specialized cardiomyocytes capable of self-exciting with regular periodicity. The natural pacemaker cells make up the cardiac pacemaker (i.e., the natural pacemaker) of the heart and directly control the heart rate. Generally, in a normal heart, cardiomyocytes within the sinoatrial (SA) node display the fastest self-excitatory periodicity and thus serve as the sole pacemaker cells. On the other hand, cardiomyocytes within the atrioventricular (AV) node exhibit the second fastest self-excitatory periodicity and usually arises as the primary pacemaker when the SA node is damaged. Cardiomyocytes within the bundle of His show the next fastest self-excitatory periodicity followed by the remainder of the Purkinje Fibers throughout the ventricle; and hence, cells at these loci emerge as the pacemakers in the event of the SA and AV node damage. Therefore, natural pacemaker cells include cardiomyocytes within both the SA and AV nodes, as well as those within Purkinje Fibers (including the bundle of His). Moreover, in the present disclosure, the term "pacemaker cells" is also referred to cells that are artificially induced to have the pacemaker activity using the methods proposed herein. On the other hand, the term "non-pacemaker cardiomyocytes" as used throughout the present disclosure are cardiac muscle cells that exhibit no self-excitatory behavior in their natural locus within the heart. For examples, the cardiomyocytes making up the atria and the ventricles are non-pacemaker cardiomyocytes.

Regarding the term "sinoatrial node-like (or SAN-like) cells," it is used herein to designate cells artificially derived from non-pacemaker cardiomyocytes. For example, the cells may be obtained from non-pacemaker cardiomyocytes by the method disclosed in the present disclosure. These SAN-like cells are capable of self-exciting. In preferred, optional embodiments, the SAN-like cells express one or more cell markers of SAN cells that are generally expressed in a low level or not expressed in the non-pacemaker cardiomyocytes. Still optionally, one or more characteristics of the self-excitation pattern of these SAN-like cells are similar or equivalent to that of the normal SAN cells.

As used herein, the term "silk fibroin" or "fibroin" includes silkworm fibroins and silk proteins from arthropods (e.g., spiders, scorpions, and mites) or insects (e.g., bees), or genetically engineered silks (such as silks from bacteria, yeast, mammalian cells, transgenic animals, and transgenic plants). Silk consists of the fibroin and sericin, in which the fibroin serves as the structural center of the silk with the sericin being the gum coating the fibers, thereby sticking them with each other. For example, silk from silkworms (*Bombyx mori*) consists of about 70 to 80% fibroin and 20 to 30% sericin, and currently is the most common source of silk fibroin. Silk fibroin can be attained by removing the sericin from the silk; a process known as degumming. Examples of conventional degumming processes include boiling the silks in an aqueous solution containing an alkaline sodium salt such as sodium carbonate or sodium bicarbonate, immersing the silks in pressurized hot water (ex. hot water of 120° C.), and enzymatic degumming. The degummed fibers may be further processed into various silk fibroin biomaterials. For example, the degummed fibers may be dissolved to give an aqueous silk fibroin solution. When further processed together with one or more suitable biocompatible polymers, the silk fibroin solution may be made into non-woven silk fibroin mats, silk fibroin films, silk fibroin hydrogels, or silk fibroin scaffolds. On the other hand, the degummed fibers may be directly made into silk fibroin cords or non-woven silk fibroin mats. Also, the silk fibroin or the silk fibroin biomaterials can be chemically modified with various active agents to alter the physical and/or chemical properties, as well as the functionalities, of the silk fibroin or the silk fibroin biomaterials.

The terms "treatment" and "treating" as used herein may refer to a preventative (e.g., prophylactic), curative or palliative measure. In particular, the term "treating" as used herein refers to the application or administration of the present pacemaker cells, a pharmaceutical composition comprising the same, or a silk fibroin biomaterial to a subject, who has a medical condition (e.g., cardiac arrhythmia), a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing the pathology associated with the disease, disorder and/or condition.

The terms "subject" and "patient" are used interchangeably herein and are intended to mean an animal including the human species that is treatable by the pacemaker cells, pharmaceutical compositions comprising the same, silk fibroin biomaterials, and/or methods of the present invention. Accordingly, the term "subject" or "patient" comprises any mammal, which may benefit from the present disclosure. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human. In one exemplary embodiment, the patient is a human. The term "subject" or "patient" intended to refer to both the male and female gender unless one gender is specifically indicated.

The terms "application" and "administration" are used interchangeably herein to mean the application of the pacemaker cells, pharmaceutical compositions, or silk fibroin biomaterials of the present invention to a subject in need of such treatment.

The term "effective amount" as used herein refers to the quantity of an agent (e.g., the present induced pacemaker cell, pharmaceutical composition, or silk fibroin biomaterial) that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed in any suitable ways. For pacemaker cells, the effective amount may be expressed as the total number of cells or cells per volume. As to the effective amount of the pharmaceutical composition, it may be expressed, for example, as the total mass (e.g., in grams, milligrams, or micrograms) or volume (e.g., in liters, milliliters, or microliters) of the medicament, a ratio of mass of the medicament to body mass (such as, milligrams per kilogram (mg/kg)), or the total number of cells or cells per volume comprised in the medicament. Regarding the effective amount of the silk fibroin, it may be expressed in grams, milligrams or micrograms. In the case where the silk fibroin is provided in the form of a solution, hydrogel, or where suitable, the effective amount of the silk fibroin may be expressed in percentage by weight (wt %), mass-to-volume percentage (% m/v), or percentage by volume (vol %).

The phrase "pharmaceutically acceptable carrier" as used herein means a pharmaceutically acceptable material, composition or vehicle, such as a liquid or solid filler, diluent, carrier, solvent or encapsulating material, involved in carrying or transporting the subject ingredients (e.g., pacemaker cells or silk fibroin) from one organ or portion of the body, to another organ or portion of the body. Each carrier must be "acceptable" in the sense of being compatible with the other ingredients of the formulation. The pharmaceutical formulation contains the pacemaker cells of the invention in combination with one or more pharmaceutically acceptable carriers for the pacemaker cells. The carrier can, for example, be in the form of a semi-solid or liquid diluent. These pharmaceutical preparations are a further object of the invention. Usually, the amount of active ingredients is between 0.1-95% by weight of the preparation. For the clinical use of the methods of the present invention, the pharmaceutical composition of the invention is formulated into formulations suitable for the intended route of administration, such as via injection. In some examples, the pharmaceutically acceptable carrier comprises the silk fibroin biomaterials (such as the silk fibroin solution or hydrogel).

The present disclosure is based, at least in part, on the unexpected discovery that the silk fibroin treatment may induce the transformation of non-pacemaker cardiomyocytes into pacemaker cells resembling natural sinoatrial node (SAN) cells. In view of the foregoing, the present disclosure provides methods for generating pacemaker cells from a cell population comprising non-pacemaker cardiomyocytes, by treating the cell population with a silk fibroin biomaterial. Some embodiments of the present disclosure are directed to methods for treating disorders associated with cardiac arrhythmia. Also provided herein is the use of aforementioned pacemaker cells or silk fibroin biomaterials in the treatment of cardiac arrhythmia, as well as for use in the manufacture of a medicament for said treatment purpose. The pacemaker cells generated using the proposed method are, of course, the subject matter covered by the scope of the present application. Further, the above-mentioned medicament (i.e., a pharmaceutical composition comprising the pacemaker cells or silk fibroin biomaterials or both) is also within the scope of the present application.

The present disclosure is advantageous in at least the following aspect. First, silk fibroins biomaterials are safe for animals, including human, and hence, they are suitable for use not only in vitro but also in vivo and ex vivo. Further, silk fibroins may be made into various forms of biomaterials depending on the use and/or application route thereof, which greatly increases the applicability of the present method. Also, the silk fibroin is an abundant resource that is readily accessible with a relatively inexpensive, as compared with stem cell therapies or gene therapies. Moreover, the preparation methods of different silk fibroins biomaterials are readily standardizable, providing a stable and reliable means for carrying out the present method.

In view of the foregoing, the first aspect of the present disclosure is directed to a method for generating pacemaker cells (or SAN-like cells).

According to some embodiments of the present disclosure, the method comprises the step of contacting a cell population comprising non-pacemaker cardiomyocytes with an effective amount of a silk fibroin biomaterial.

As could be appreciated, the present method may be carried out in vitro, in vivo, or ex vivo. In the case where the population of cells and the silk fibroin biomaterial are contacted in vitro, the method further comprises the step of culturing the population of cells with the silk fibroin biomaterial so that one or more of the non-pacemaker cardiomyocytes are transformed into the pacemaker cardiomyocytes or SAN-like cells. For instance, the population of cells and the silk fibroin biomaterial are cultured in a medium suitable for the cells, and then placed under a condition that facilitates the growth, proliferation and/or transformation of the cells. As to the ex vivo culture, the population of cells or the tissue or organ comprising the non-pacemaker cardiomyocytes is contacted with the silk fibroin biomaterial under a condition sufficient to transform one or more of the non-pacemaker cardiomyocytes into pacemaker cells. For in vivo transformation of the cells, the silk fibroin biomaterial is applied to the target site within a subject's body; in particular, the silk fibroin biomaterial is formulated in a form that increases the retention of the silk fibroins at the target site, so that a sufficient number of non-pacemaker cardiomyocytes at the target site are transformed into pacemaker cells under the induction of silk fibroins.

According to various optional embodiments of the present disclosure, the above-mentioned non-pacemaker cardiomyocytes may be atrial and ventricular cardiac muscle cells.

As could be appreciated, these cardiac muscle cells do not generate electrical impulses (or action potentials) spontaneously in their natural locus within the heart, and hence the name "non-pacemaker cardiomyocytes."

The silk fibroin biomaterial may be made into different forms depending on the setting in which the silk fibroin biomaterial is used, as long as they allow an adequate contact between the silk fibroin biomaterials and the cells to be treated. According to some embodiments of the present disclosure, aqueous solutions (SF solutions) containing about 0.1 to 50% (w/w) silk fibroins are used. Specifically, the SF solutions may contain about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, or 50% (w/w) silk fibroins. Alternatively, silk fibroin particles (SF particles) having an average diameter in the range of about 50 nm to 10 mm are administered to the cells; for examples, the cells and the SF particles may be mixed in vitro or ex vivo. Preferable, the average diameter of SF particles may be 100 nm to 5 mm; more preferably, 200 nm to 1 mm, 500 nm to 500 µm, 1 µm to 100 µm, or 10 µm to 50 µm. Still alternatively, the silk fibroin biomaterials may be made into non-woven silk fibroin mats (SF non-woven mats) or silk fibroin scaffolds (SF scaffolds); these biomaterials have a three-dimensional structure with an increased surface area, which facilitates the retention of cells. For example, the SF non-woven mats or SF scaffolds may be used to culture and transform the cells in vitro, and then, the thus-generated pacemaker cells are collected and administered to a subject.

Alternatively, the pacemaker cells are administered to the subject along with the silk fibroin biomaterials. As another example, the SF non-woven mats or scaffolds may be administered to the target site of the subject and then induce the transformation of non-pacemaker cardiomyocytes into pacemaker cells in situ. Likewise, silk fibroin hydrogels (SF hydrogels) and silk fibroin films (SF films) also promote the retention of cells, as well as prolong the residence of the biomaterials at the target site. Accordingly, SF hydrogels or SF films may be used for in vitro or ex vivo culture or in vivo induction, or a combination thereof.

According to certain embodiments of the present disclosure, a silk fibroin film is provided. The SF film comprises a biodegradable polymeric film, which is chemically modified to increase the amines group on the surface thereof, and a plurality of silk fibroins crosslinked with the biodegradable polymeric film via the amine groups. As could be appreciated, a thin film of silk fibroin may also be formed by coating an SF solution or SF hydrogel (or a liquid or gel containing SF particles dispersed therein) on to the surface of a suitable article (such as, a glass slide, a plastic or metal (e.g., stainless steel) sheet, or a syringe needle), and then allowing the continuous phase to evaporate, thereby obtaining the SF film.

In another aspect, the present invention is directed to pacemaker cells generated using any of the methods described above. According to optional embodiments of the present invention, the pacemaker cells are SAN-like cells that exhibit an increased expression level of HCN4 gene or connexin 45 gene, or both, compared with the cells that are not transformed. Still optionally, the SAN-like cells exhibit sinoatrial node-specific calcium clock. Also, according to certain embodiments, the morphology of the SAN-like cells is similar to that of the natural pacemaker cells.

In yet another aspect, the present disclosure is directed to a pharmaceutical composition for treating cardiac arrhythmia in a subject in need of such treatment. According to certain embodiments of the present disclosure, the pharmaceutical composition comprises an effective number of pacemaker cells and a pharmaceutically acceptable carrier for the pacemaker cells. In optional embodiments, the pharmaceutical composition further comprises an effective amount of a silk fibroin biomaterial. For example, the silk fibroin biomaterial may be in the form of a silk fibroin solution, a silk fibroin particle, a non-woven silk fibroin mat, a silk fibroin hydrogel, a silk fibroin film, or a silk fibroin scaffold. According to certain embodiments, the pacemaker cells and the silk fibroin biomaterial may be formulated into a single composition or separately into two compositions.

According to various embodiments of the present disclosure, the pharmaceutical composition may be formulated into a dosage form suitable for the desired mode of administration. As could be appreciated, the pacemaker cells can be administered into any area of the heart where conduction disturbances have occurred. The number of pacemaker cells necessary to be therapeutically effective varies with the type of disorder being treated as well as the extent of the overall damage of myocardial tissue, among other factors. A particularly suitable administration mode can be in situ application of the present pacemaker cells or pharmaceutical composition to a cardiac tissue by, for example, direct surgical application. Another particularly suitable administration mode can be catheter injection of the present pacemaker cells or pharmaceutical composition to a cardiac tissue. There have been many known techniques that can be used to facilitate the access to the administration site. For example, the catheter injection may be used in connection with a fluoroscopy, X-ray, echocardiography, or magnetic resonance imaging guiding system. It should be noted that the above-mentioned administration routes are provided for the purpose of discussion, and the present disclosure is not limited to these administration modes. Rather, according to some embodiments, the pacemaker cells, silk fibroin biomaterials, or pharmaceutical compositions may be administered systemically. Illustrative examples of dosage forms of the pharmaceutical composition include suspensions, dispersions, solutions, ointments, pastes, powders, dressings, creams, and gels. As could be appreciated, these pharmaceutical compositions are also within the scope of the present disclosure.

In still another aspect, the present disclosure is directed to a method for treating a subject suffering from cardiac arrhythmia.

In some embodiments, the treatment method comprises the step of administering to the subject an effective number of the present pacemaker cells or a pharmaceutical composition comprising the same. Alternatively, the treatment method comprises the step of administering to the subject an effective number of silk fibroin biomaterial or a pharmaceutical composition comprising the same, so that the silk fibroin biomaterial induces the formation of pacemaker cells from non-pacemaker cardiomyocytes within the heart of the subject. Still alternatively, the treatment method comprises the step of administering to the subject an effective number of the present pacemaker cells and the silk fibroin biomaterial to the subject. As could be appreciated, the pacemaker cells and the silk fibroin biomaterial may be formulated in a single pharmaceutical composition or two separate pharmaceutical compositions; in the latter case, the two pharmaceutical compositions may be administered to the subject simultaneously or separately.

In some embodiments, about 1 µl to 500 µl of SF hydrogel (prepared using a 0.1-50% (w/w) SF solution) is administered to a rat subject; optionally, the SF hydrogel may be administered to a rat at a dose of about 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, or 500 µl. According to optional embodiments of the present disclosure, in the case where the subjects are humans, about 100 µl to 250 ml of SF hydrogel (prepared using a 0.1-50% (w/w) SF solution) may be administered. For human administration, the dose of the SF hydrogel may be about 100, 110, 120, 130, 140, 150, 160, 170, 180, 190, 200, 250, 300, 350, 400, 450, 500, 550, 600, 650, 700, 750, 800, 850, 900, or 950 µl, or 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, or 250 ml.

As to the SF solution (0.1-50% (w/w)), about 10 to 500 µl of SF solution is administered to the rat; for example, the rat dose of the SF solution may be 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, or 500 µl. Regarding the human subject, the dose of the SF solution (0.1-50% (w/w)) may be in the range of 1 to 250 ml, such as 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, or 250 ml. According to various embodiments of the present disclosure, the concentration of the SF solution is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 20, 25, 30, 35, 40, 45 or 50% (w/w).

As to the silk fibroin biomaterials in other forms, the dose of these silk fibroin biomaterials may be estimated from the silk fibroin content in the above-mentioned dose of the SF solution or SF hydrogel. Generally, the content of the silk fibroin in other forms of silk fibroin biomaterials may be equivalent as or similar to the silk fibroin content in the SF solution or SF hydrogel.

In the case where the pacemaker cells are administered to a human subject, the effective amount is about 100 to 1,000,000 viable pacemaker cells; preferable, about 1,000 to 100,000 viable pacemaker cells.

The above-mentioned suitable doses for experimental animals are determined from the experimental data provided herein, whereas the equivalent doses for human subjects can be decided by considering the differences in the weight, volume, and/or surface area of the hearts between the experimental animal and a human subject. As could be appreciated, the above-mentioned effective amount may be administered in a single dose or split into several doses that are administered over a suitable time period at desired time interval.

According to some preferred, optional embodiments of the present disclosure, the population of non-pacemaker cardiomyocytes used to generate the pacemaker cells is derived from the subject to be treated. However, the present invention is not limited thereto.

Also include in the scope of the presently claimed invention are use of a silk fibroin biomaterial or pacemaker cells for the manufacture of a medicament that can be used in treating cardiac arrhythmia.

The following Examples are provided to elucidate certain aspects of the present invention and to aid those of skilled in the art in practicing this invention. These examples are in no way to be considered to limit the scope of the invention in any manner. Without further elaboration, it is believed that one skilled in the art can, based on the description herein, utilize the present invention to its fullest extent.

Materials and Methods (1) Preparation of Silk Fibroin Solution

Briefly, *Bombyx mori* cocoons were cut into small pieces and boiled in a 0.02 M aqueous solution of sodium carbonate ($Na_2CO_3$) for 90 minutes to remove sericin. The resulting fiber bundles were rinsed with deionized water and air-dried at room temperature. The dried fiber bundles were then mixed with a 9.3 M aqueous solution of lithium bromide (LiBr) in an adequate amount, the reaction mixture is reacted under about 70 to 80° C. for 1 hour to prepare a 20% (w/w) silk fibroin (SF)/LiBr solution. The resulting SF/LiBr solution was then centrifuged (approximately 4,500 to 8,000 G for around 10 minutes) and filtered via microfiltration to remove any residual impurities. The SF/LiBr solution was then dialyzed in dd$H_2O$ using a cellulose dialysis tubing with a molecular weight cutoff of 6,000 to 8,000 Da for 3 days. When the pH of the solution within the dialysis tubing was less than 7, it was determined that the solution was free of LiBr, thereby obtaining the silk fibroin (SF) solution, which was stored at 4° C. before use. The gravimetric measurement indicated that the concentration of silk fibroin in the thus-obtained fresh SF solution was about 3-4% (w/w).

(2) Preparation of Silk Fibroin Film

Poly(ε-caprolactone) (PCL; molecular weight 80 kDa, from Sigma, St. Louis, MO, USA) was dissolved in tetrahydrofuran (THF) at a concentration of 20%. The PCL/THF solution was casted on a glass coverslip, evaporated, and a PCL film was formed using a spinning-coating machine (1,000 to 2,000 G for 1 minutes), thereby forming the PCL film with a thickness of about 3 to 10 µm. The dried PCL film was then treated with poly(ethylamine) (molecular weight: 800 Da, Sigma, St. Louis, MO, USA) to increase the amount of surface amino groups on the PCL, followed by cross-linking a thin layer of 1% SF solution with 1% glutaraldehyde for several minutes. After air-dried at the room temperature, the SF films with 20% to 40% crystallinity were first prepared. To prepare SF films with more than 40% crystallinity, the SF film with 20% to 40% crystallinity was dipped into 95 to 100% ethanol for several minutes to induce β-sheet formation. To assure the successfully grafting of SF onto the PCL surfaces, photochemical reactions were performed on the surface of the SF film. Briefly, 200 µl of N-succinimidyl-6-[4'-azido-2'-nitrophenyl-amino]-hexanoate (SANPAH; molecular weight: 492.4 Da, Pierce Chemical) in ethanol solution was gently added onto a SF film, which was placed in a dark room for several hours to allow the formation of produce azido-derivative reactants, and the surface was then irradiated with 60 W UV light (290 to 370 nm) for 3 to 5 minutes.

(3) Preparation of Silk Fibroin Hydrogel

Horseradish peroxidase (HRP) (type VI, lyophilized powder; from Sigma-Aldrich, St. Louis, MO) was mixed with deionized water to form a stock solution with a concentration of 1,000 U/mL. The HRP solution was then added to the above-mentioned SF solution in a ratio of 10-20 Units of HRP to 1 mL of the SF solution. To initiate the gelation, 0.1-0.2 µl of 30% hydrogen peroxide (Sigma Aldrich, St. Louis, MO) solution was added into 1 mL of the HRP-SF solution (final concentration of hydrogen peroxide: about 0.003 to 0.006%), and mixed by gentle pipetting prior to setting.

(4) Isolation and Seeding of Cardiomyocytes

Neonatal rat ventricular myocytes (NRVMs) were isolated from neonatal rat (1- to 2-day old) pups. The pups were decapitated first, and then dipped into 70% ethanol. To isolate the cardiomyocytes, the rib cage of pups was opened and the heart was exposed. The cut-off ventricle placed in HBSS buffer on ice was then cut into smaller pieces and incubated with 0.25% trypsin/HBSS in the flask overnight on shaker at 4° C. After aspirating the trypsin, the medium was added into the flask and incubated for 20 minutes at 37° C., the medium was then removed and replaced with collagen. The supernatant was collected and centrifuged at 50 G for about 10 minutes. To remove the un-isolated tissue, the cell suspension was filtered with a 70-µm strainer and centrifuged at 50 G for 5 minutes, and then re-suspended in the medium. The cell suspension was placed into a T175-flask and incubated at 37° C. for 2 hours to allow the un-wanted fibroblast to adhere. The cells were collected and the NRVMs were seeded onto the fibronectin-coated cover slide or the SF film at a proper cell density.

(5) Calcium Imaging by Confocal Microscopy

Seeded cardiomyocytes in Tyrode's solution were loaded with $Ca^{2+}$ indicators (10 µM Fluo-3/AM for cardiomyocytes; Calbiochem, San Diego, CA, USA) and incubated at room temperature for 30 minutes in the dark. Fluorescence imaging was performed with a laser scanning confocal microscope (Olympus IX71, Olympus America). The fluorescence density (F) was normalized against the baseline fluorescence ($F_0$) to determine the transient $[Ca^{2+}]_i$ changes, which had excluded variations in the fluorescence intensity because of different volumes of injected dye. Offline analysis was performed using Olympus IX71 and ImageJ.

(6) Immunostaining of Cardiomyocytes

Cardiomyocytes were fixed with 4% paraformaldehyde and permeabilized with 0.1% Triton-X 100 and then incubated with the appropriate primary antibody: sarcomeric α-actinin (Sigma-Aldrich), HCN4 (Alomone), beta1 adrenergic receptor (Abcam), muscarinic acetylcholine receptor 2 (Abcam) and Alexa Fluor-conjugated secondary antibodies (Invitrogen). Morphometric assays were performed with ImageJ by measuring the cell length (short and long-axis) of each cardiomyocytes.

(7) Real-Time Polymerase Chain Reaction (RT-PCR)

Total RNA was extracted from seeded cardiomyocytes using an RNeasy® Mini Kit (QIAGEN, Venlo, Netherlands). cDNA was synthesized using a SuperScript® III First-Strand Synthesis System (Invitrogen, Carlsbad, CA, USA). Real-time quantitative PCR was performed using a Roche LightCycler® 480 Real Time PCR system with a Taqman Master Mix reagent. The primers for the genes of interest (HCN4, Rn00572232_m1; Cx45 (Gjc1), Rn01750705_m1; ANP (Nppa), Rn00561661_m1; Myl2, Rn01480558_g1; NKx2.5, Rn00586428_m1; Acta1, Rn01426628_g1; Tbx18, Rn01445129_m1; Shox2 Rn00564672_m1; GAPDH, Rn01775763_g1) were from Invitrogen (Carlsbad, CA, USA).

(8) Patch Clamp Analysis

Spontaneous action potentials and currents of cardiomyocytes were recorded at 37° C. in the perforated patch configuration using a Axon CNS 700B amplifier (Molecular Devices, CA, USA) and the pClamp software (version 10; Molecular Devices). The offline data analysis was conducted with Clampfit software (Molecular Devices, CA, USA) or by means of Origin 6.0 software (Microcal, Northampton, USA). Patch pipettes were drawn from borosilicate glass and heat-polished, and had a resistance of 2-5 MΩ on filling with intracellular solution which contained 10 mM NaCl, 130 mM potassium aspartate, 0.04 mM $CaCl_2$, 3 mM Mg-ATP, 10 mM HEPES and 200 µg/ml amphotericin B, pH adjusted to 7.2 with KOH. The extracellular (bath) solution contained 140 mM NaCl, 5.4 mM KCl, 1 mM $MgCl_2$, 1.8 mM $CaCl_2$, 5 mM HEPES, 5.5 mM glucose; the pH was adjusted to 7.4 with NaOH. Action potentials (APs) were recorded with a 10-kHz sampling rate.

(9) Animals

Rats were supplied by National Laboratory Animal Center (Taiwan). All animals used in working examples of the present disclosure were housed in an animal room under temperature control (24-25° C.) and 12:12 light-dark cycle. Standard laboratory chow and tap water were available ad libitum. The experiments procedures were approved by the Institutional Review Board of Taipei Veterans General Hospital (Taipei, Taiwan) and were performed in compliance with national animal welfare regulations.

(10) Statistical Analysis

Data were analyzed for mean, standard deviation (s.d.), and standard error of the mean (s.e.m. or SEM). The quantitative figures in this work represent the mean±SEM. Unless indicated otherwise, data sets were statistically evaluated using a two-tailed t test, and confidence level of $P<0.05$ was considered significant.

Example 1

SF Increases Automaticity in Neonatal Cardiomyocytes

The NRVMs ($5 \times 10^4$ cells) were seeded on coverslips coated with fibronectin (control) or the above-mentioned SF film. Three to five days after seeding, the number of spontaneously beating cardiomyocytes were counted, and incidence of beating cardiomyocytes was calculated as follows: (number of beating cardiomyocytes)/(total number of cardiomyocytes)*100%.

Figure 1B:
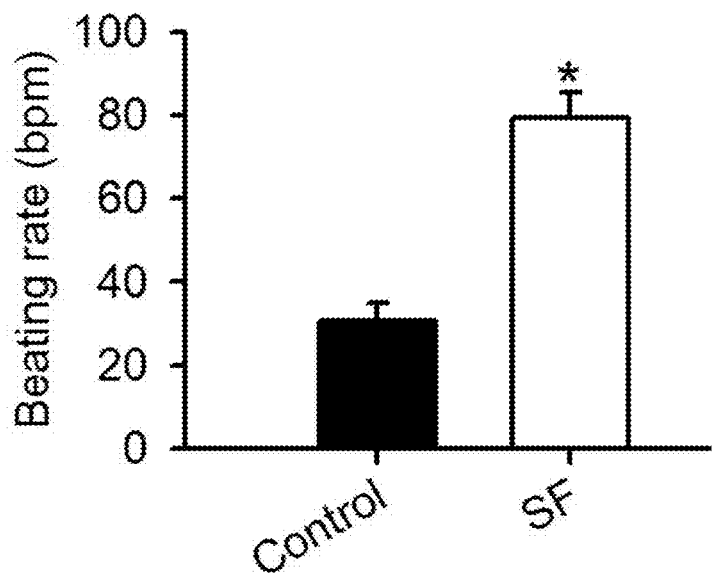

The results, as summarized in FIG. 1A, indicated that the number of spontaneously beating NRVMs on the present SF film was greater than that in control groups, and the difference was statistically significant (SF, n=184; control, n=239; *P<0.001; 5 independent experiments). Also, as shown in FIG. 1B, the beating rate of beating foci in SF-treated groups was higher than that in control groups (SF, n=50; control, n=51; *P<0.001; 5 independent experiments).

Figure 1C:
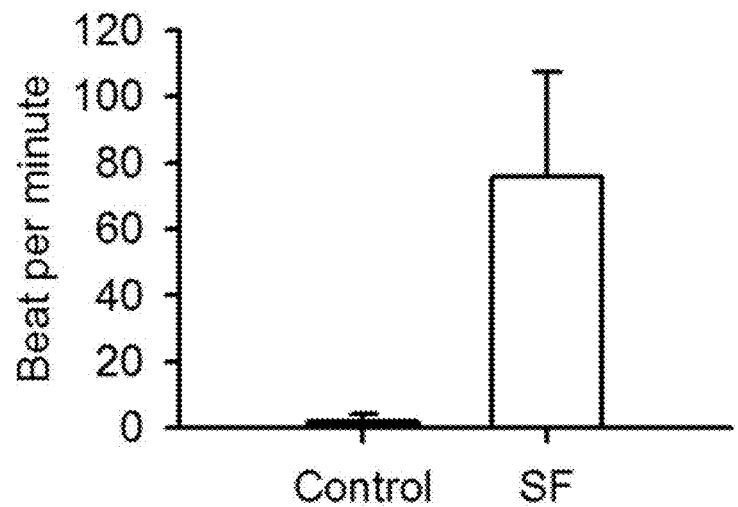
FIG. 1C and FIG. 1D are bar graphs respectively illustrating the beating rate in cardiomyocytes treated with SF solution and SF hydrogel, compared with PBS control, according to one working example of the present disclosure.

NRVMs ($5 \times 10^4$ cells) were also treated with the SF solution (2-5% (w/w)) or PBS (control). Two to three days after the treatment, the mean heart rate (bpm) was measured. The results, as summarized in FIG. 1C indicated that in the control group, the mean heart rate was 2.0±2.0 bpm, whereas in the cells treated with the SF solution, the mean heart rate was 76.0±31.3 bpm.

Figure 1D:
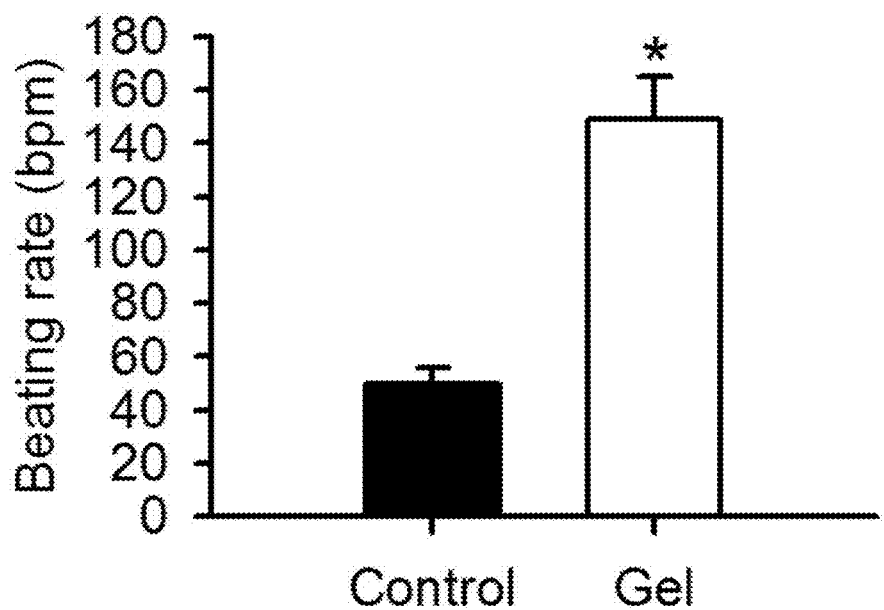

For SF hydrogel, NRVMs ($5 \times 10^4$ cells) were treated with the SF hydrogel prepared using 2-3% (w/w) SF solution or PBS (control). Three to five days after the culturing, the mean heart rate (bpm) was measured. The results, as summarized in FIG. 1D indicated that in the control group, the mean heart rate was 49.6±6.0 bpm, whereas in the cells treated with the SF hydrogel, the mean heart rate was 149.1±16.0 bpm (P<0.05).

These data established that the present SF-treatment was effective in inducing the transformation of ventricular cardiomyocytes into pacemaker cells that beat spontaneously.

Example 2

Distinguished Transcriptional Gene Signatures of SAN Cardiomyocytes in SF-Treated Cardiomyocytes It is well-known that many types of cells exhibit a gene signature in which certain unique genes are expressed in higher levels, as compared with those of the same genes in other types of cells. For example, HCN4 and Connexin 45 (Cx45) genes, among others, are SAN-specific genes highly expressed in mature SAN cells. On the other hand, ANP and Myl2 genes are markers of ventricular cardiomyocytes. Also, there are some cardiac-specific markers (e.g., ACTA1 and NKX2.5) that are expressed in cardiomyocytes with de-differentiation. Therefore, in this working example, mRNA levels of the aforementioned genes in SF-treated cardiomyocytes (from Example 1) were determined to investigate whether the genetic expression profile of SF-treated cardiomyocytes bear resemblance to that of the native mature SAN cells, or whether they retain the genetic expression profile of ventricular cardiomyocytes.

Figure 2A:
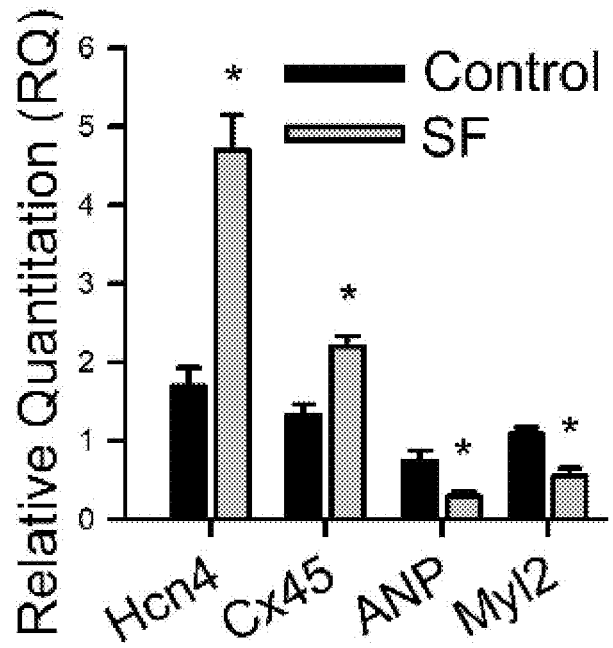
FIG. 2A and FIG. 2B are bar graphs illustrating the relative quantitation of different marker genes in cardiomyocytes, according to one working example of the present disclosure.
Figure 2B:
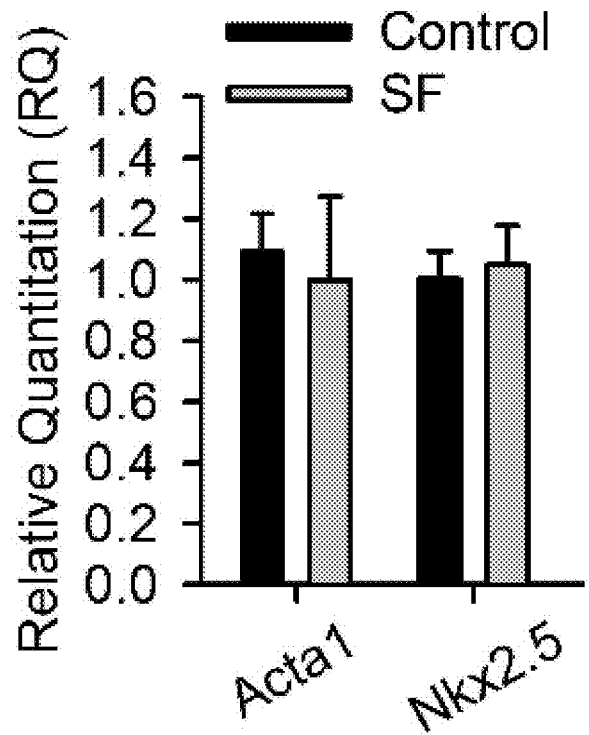

As could be seen in FIG. 2A, mRNA expression levels of HCN4 and Cx45 in SF-treated cardiomyocytes were statistically higher than those of the control groups. On the other hand, the mRNA expression levels of ANP and Myl2 genes were significantly lower in SF-treated cardiomyocytes. Specifically, the SF-treated cardiomyocytes exhibited a 3-fold increase in HCN4 mRNA level and 2-fold increase in Cx45 mRNA level, while the mRNA levels of ANP and Myl2 in SF-treated cardiomyocytes decreased more than 3 folds (n=7-12, *P<0.05). In contrast, the expression of Acta1 and Nkx2.5 in SF-treated cardiomyocytes were not significantly different from those in control cardiomyocytes (FIG. 2B, P=0.76 for Acta1, and P=0.77 for Nkx2.5, n=7). This indicated the automaticity in SF-treated cells is not associated with de-differentiation.

Figure 2C:
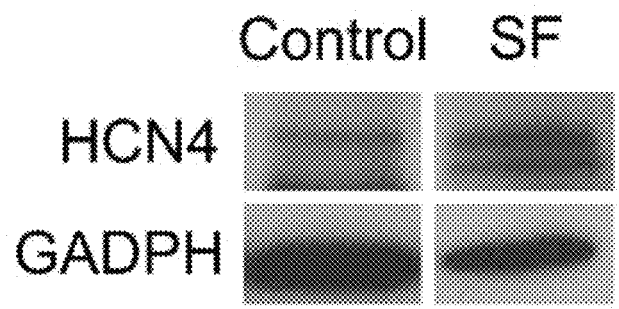
FIG. 2C is a western blot for HCN4, according to one working example of the present disclosure.
Figure 2D:
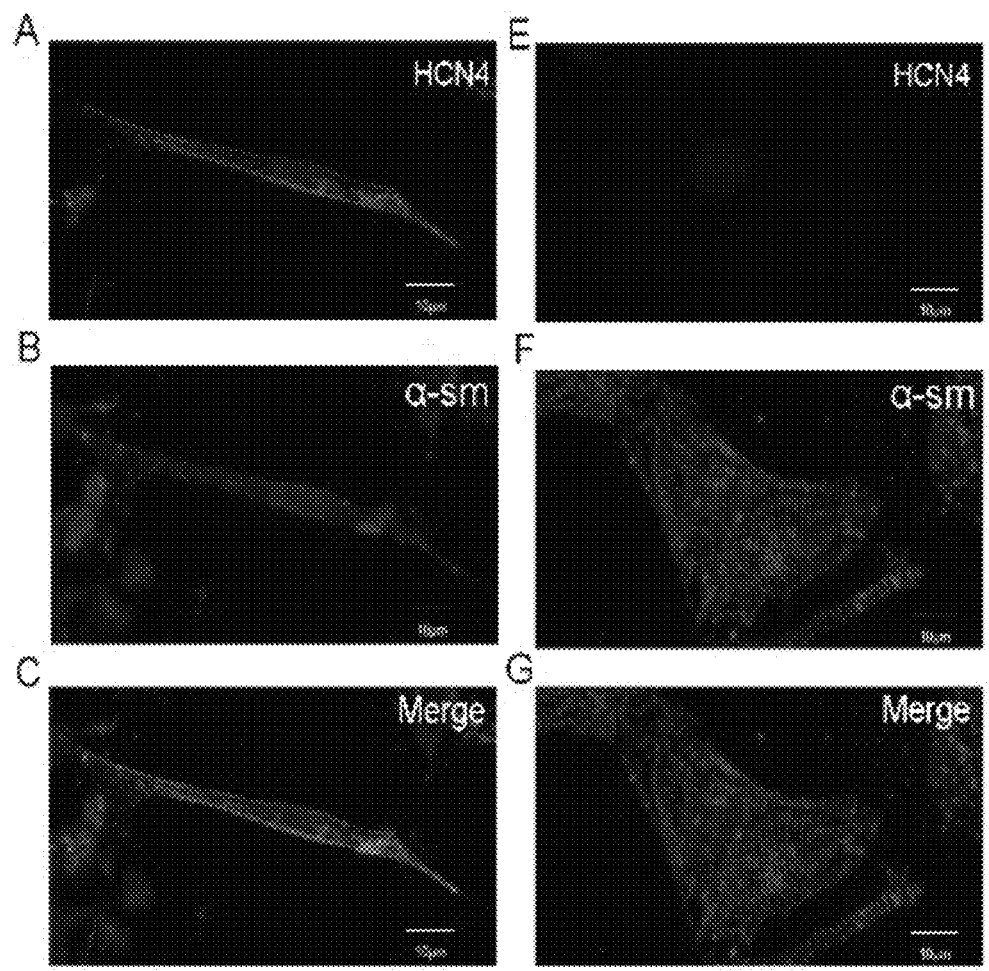
FIG. 2D presents immunostaining images of cardiomyocytes, according to one working example of the present disclosure.

The expression of HCN4 in SF-treated cardiomyocytes was further confirmed by western blotting (FIG. 2C) and immunostaining (FIG. 2D). The representative western blot in FIG. 2C indicated the increased expression of HCN4 was seen in SF-treated cardiomyocytes, as compared with that of the control cells. As can be seen in representative immunostaining photographs in FIG. 2D, significant HCN4 expression (green fluorescence) was found in SF-treated cardiomyocytes (panels A and C), whereas the level of HCN4 was not detectable in control cells (panels D and E). On the other hand, a decrease in sarcomeric α-actinin (α-sm) (red fluorescence) expression was observed in SF-treated cardiomyocytes (panels B and C), as compared with that of the control cells (panels E and F). Further, the morphological examination revealed that SF-treated cardiomyocytes had an elongated or spindle configuration, as well as myofibrillar disorganization (FIG. 2D, panels A to C); which features resembled the morphology of native SAN cells. On the other hand, control cells retained the morphology of ventricular cardiomyocytes with organized myofibrils (FIG. 2D, panels D to E). The blue fluorescence in the immunostaining photographs are stained by DAPI.

Experimental data in this working example evidenced that the SF treatment effectively transformed cardiomyocytes into SAN-like cells; in particular, the transformed cells were similar to native SAN cells in terms of their gene expression profile and morphology.

Example 3

SF-Treated Cardiomyocytes Exhibit Sinoatrial Node Action Potential

This working example used the patch clamp analysis to elucidate the electrophysiology of SF-treated cells.

Figure 3:
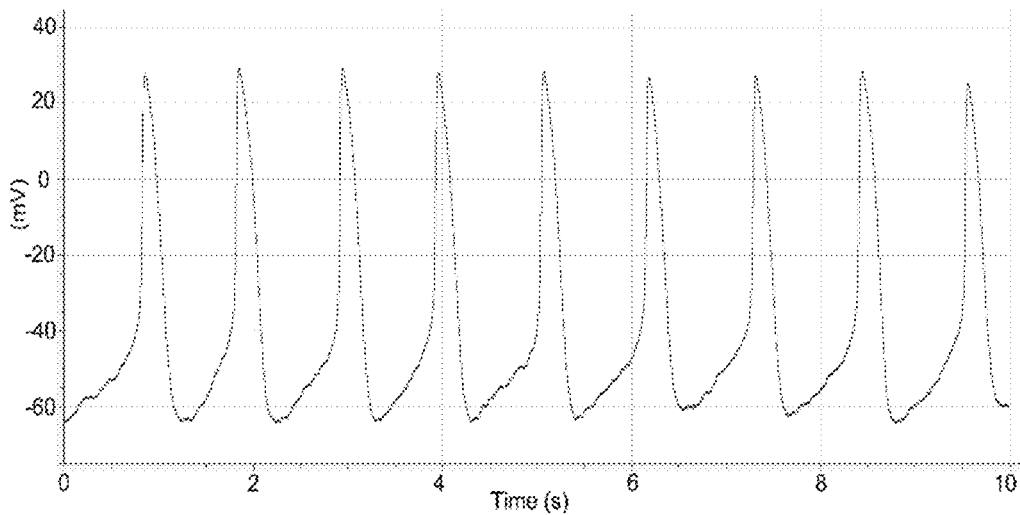
FIG. 3 is a representative diagram illustrating the action potential of cardiomyocytes over times, according to one working example of the present disclosure.

The result indicated that some of the non-pacemaker cardiomyocytes treated with SF (from 4 independent experiments) exhibited spontaneous action potentials. FIG. 3 is a representative diagram illustrating the action potential of one SF-treated cardiomyocyte over time, in which the action potential pattern exhibited a prominent phase 4 depolarization with the rest membrane potential set at about −60 mV, which resembled that of SAN cells. Also, the waveforms of SF-treated cardiomyocytes mimicked those of sinoatrial node. In contrast, cardiomyocytes on the control film required pacing to create an action potential, and no SAN-like action potential was noted (data not shown).

Example 4

SF-Treated Cardiomyocytes Exhibit Sinoatrial Node-Specific Calcium Clock

Automaticity in the SAN cell is the integration between the cyclic depolarization of action potentials and the intracellular $Ca^{2+}$ cycling. A distinct localized, sub-sarcolemmal $Ca^{2+}$ release (LCR) during the diastolic depolarization (DD) of the SAN cell is another hallmark of automaticity in SAN cells, in which the LCR augments the depolarization rate of the phase 4 action potential and is closely linked with the spontaneous cycle length. Therefore, in this example, calcium imaging was performed to investigate whether the SF-treated cardiomyocytes from Example 1 exhibited the calcium clock that is seen in normal SAN cells.

Figure 4:
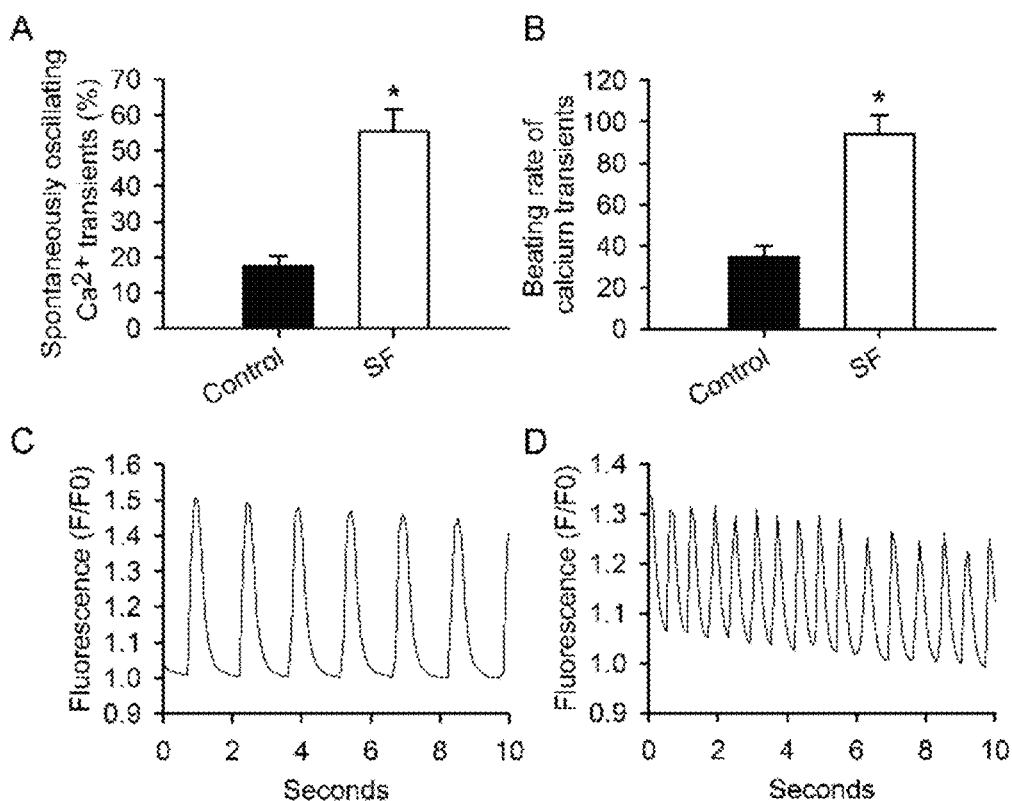
FIG. 4 presents diagrams illustrating the calcium dynamics of cardiomyocytes, according to one working example of the present disclosure.

The data in FIG. 4 indicated that a higher incidence of spontaneously oscillating calcium transients was seen in SF-treated cardiomyocytes (panel A; SF, n=11; control, n=23; P<0.001; 5 independent experiments), and a faster beating rate of calcium transients was also observed in SF-treated cardiomyocytes (panel B; SF, n=47; control, n=59; P<0.001; 5 independent experiments). Panel C and panel D in FIG. 4 are representative diagrams illustrating the calcium transient tracings of cardiomyocytes in the control group (panel C) and SF-treated group (panel D), respectively. The data in FIG. 4 demonstrated that more spontaneously oscillating calcium transients were seen in cardiomyocytes treated with SF; this result is in line with the underlying theory that calcium cycling plays a critical role in the spontaneous beating of cardiomyocytes.

Figure 5:
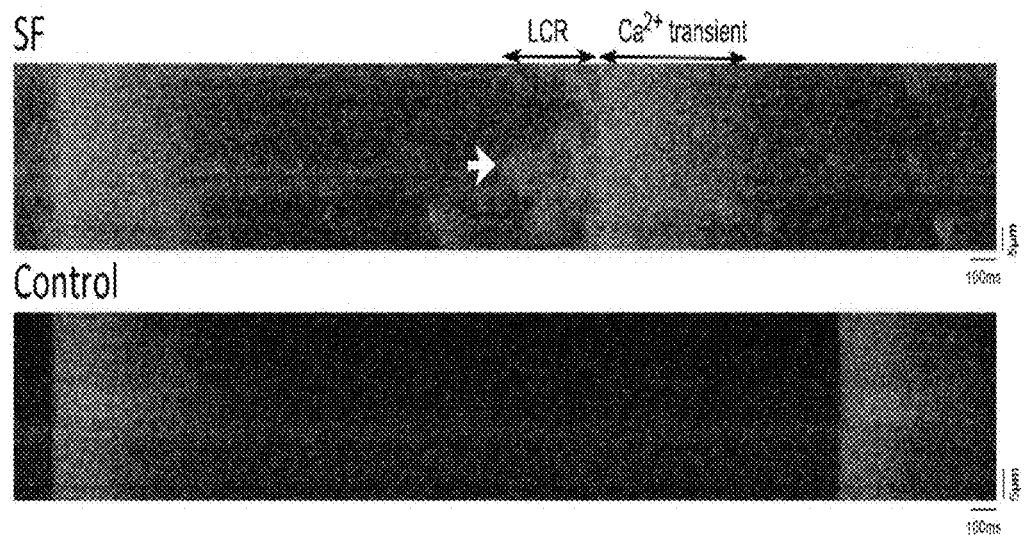
FIG. 5 is line-scan confocal imaging of cardiomyocytes, according to one working example of the present disclosure.

Further, results from the line-scan confocal imaging (FIG. 5) indicated that the LCR preceding each whole-cell $Ca^{2+}$ transient was only observed in SF-treated cardiomyocytes. Specifically, a localized, sub-sarcolemmal $Ca^{2+}$ release (LCR) was evidenced by the clustered calcium sparks (white arrow in FIG. 5) during the diastolic depolarization and before the whole-cell $Ca^{2+}$ transient. In contrast, for control cardiomyocytes, occasional and randomly distributed $Ca^{2+}$ sparks were only seen after the whole-calcium $Ca^{2+}$ transient. Moreover, the SF-treated cardiomyocytes exhibited wider and longer-lasting LCRs with higher amplitudes, as compared with the random $Ca^{2+}$ sparks seen in control cells (FIG. 5).

In sum, these data established that cardiomyocytes treated by SF displayed a distinct localized, sub-sarcolemmal $Ca^{2+}$ release profile that was similar to native SAN pacemakers. The expressions of Ryr2, Cav1.2, Ncx1, Serca2, and PLN did not differ between the control and SF treated cardiomyocytes (data not shown).

Example 5

HCN4 Inhibitor Suppresses Spontaneous Beating Rate in SF-Treated Cardiomyocytes

The spontaneous beating is tightly regulated by HCN4 channels in native SAN pacemakers. Therefore, in this example, cells from Example 1 were treated with 3 μM ivabradine, a selective HCN4 inhibitor, to evaluate the impact of HCN4 on the function of SF-treated cardiomyocytes.

Figure 6A:
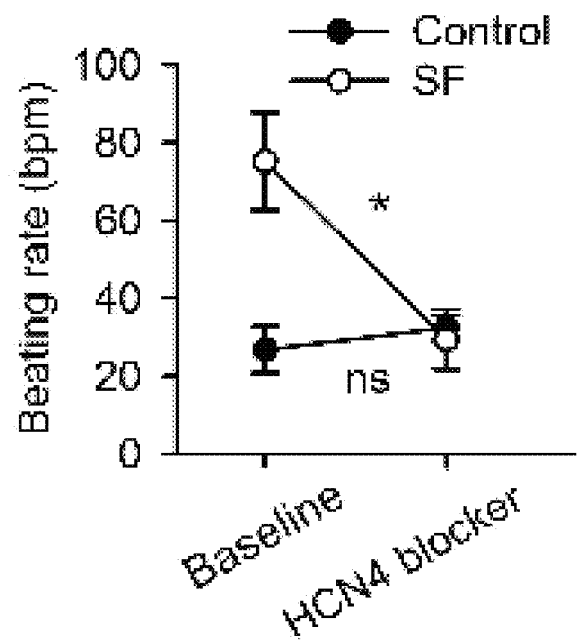
FIG. 6A is a line graph illustrating the effect of ivabradine (a selective HCN4 inhibitor) on the beating rate of the SF-treated cardiomyocytes and control cardiomyocytes, according to one working example of the present disclosure.

As shown in FIG. 6A, ivabradine suppressed the beating rate (i.e., the cycling rates of spontaneous calcium transient) of SF-treated cardiomyocytes by 57%, as compared with the baseline measurement from SF-treated cells that were not treated with ivabradine. On the other hand, the beating rates of control cells treated with ivabradine did not differ significantly from the baseline measurement of the control (SF, n=15, P=0.002; control, n=32, P=0.24; 6 independent experiments, P values were determined by paired t test).

Figure 6B:
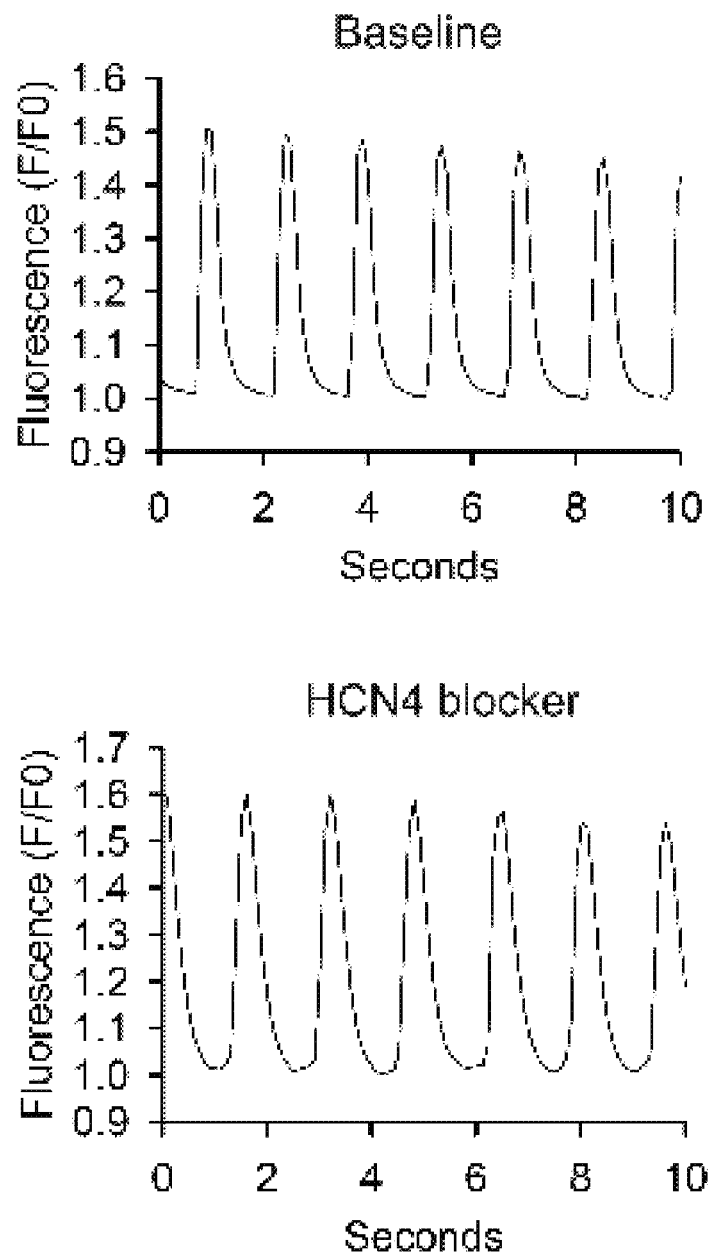
FIG. 6B and FIG. 6C respectively present diagrams illustrating the electrophysiology properties of control and SF-treated cardiomyocytes, according to one working example of the present disclosure.
Figure 6C:
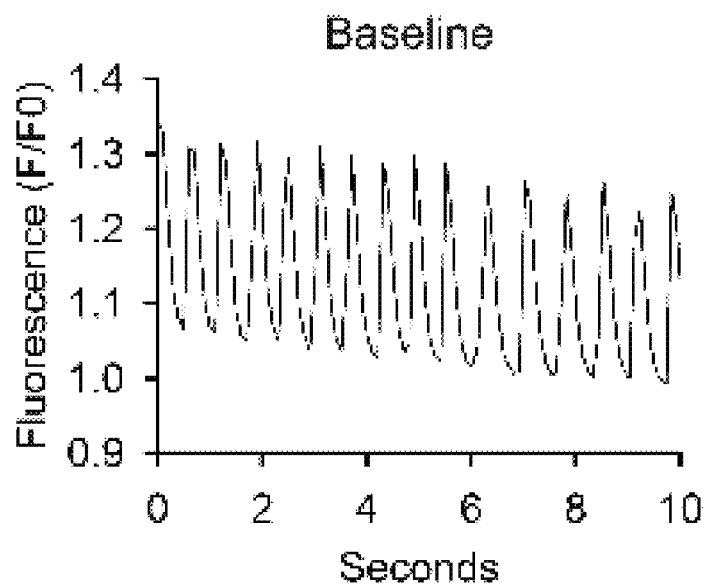
Figure 6C:
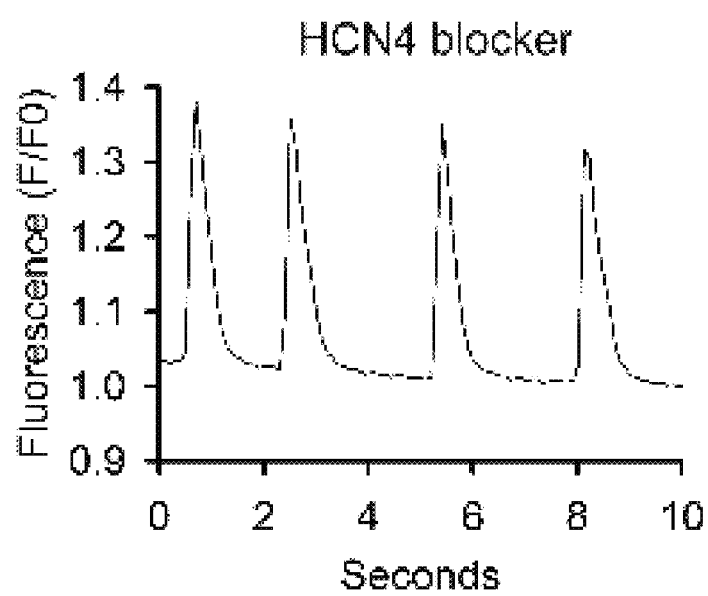

FIG. 6B and FIG. 6C are representative diagrams illustrating the calcium transient tracings of cardiomyocytes in the control group and SF-treated group. Reference in first made to FIG. 6B, which demonstrates that for control NRVMs, the administration of ivabradine did not significantly alter the rate of calcium transient (bottom panel), as compared with the baseline measurement (top panel). In contrast, as could be seen in FIG. 6C, in the SF treatment group, the rate of calcium transient of ivabradine-treated cardiomyocytes (bottom panel) was significantly lower than that of the baseline measurement (top panel).

Example 6

SF Treatment Induces Morphology Conversion of Cardiomyocytes

Figure 7:
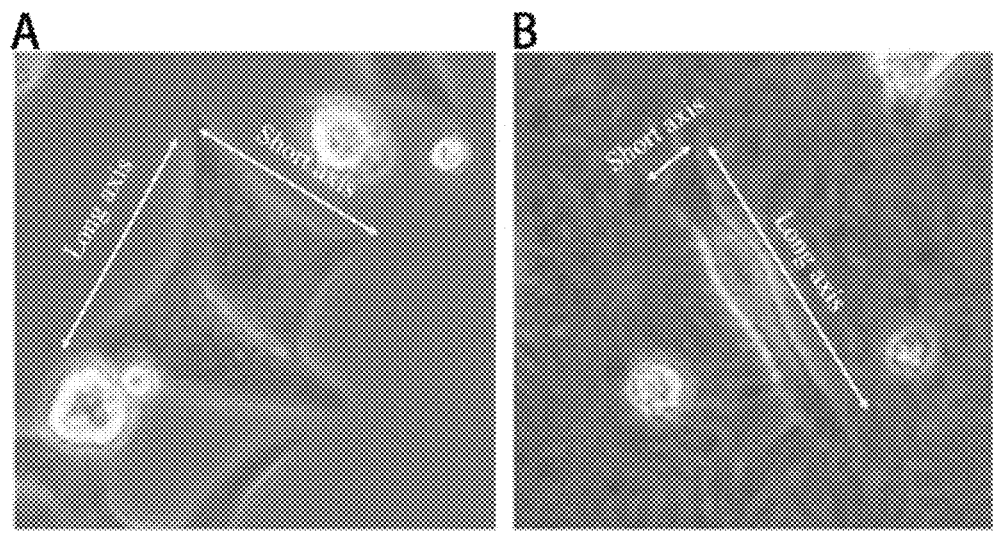
FIG. 7 provides photographs illustrating the morphology of cardiomyocytes, according to one working example of the present disclosure.

Each SAN cells had a distinct morphology that is elongated or spindle-like, while cultured ventricular cardiomyocytes often exhibited a polyhedral central body with cytoplasmic radial projections. As could be seen in panel A of FIG. 7, the control NRVM had a long axis slightly longer than the short axis and four radial projections. On the other hand, the cardiomyocyte treated with SF (from Example 1) had a long axis that was 5 times longer than the short axis, which resembled the morphology of native SAN cells; also, it lacked the radial projections (see, panel B, FIG. 7).

Figure 8:
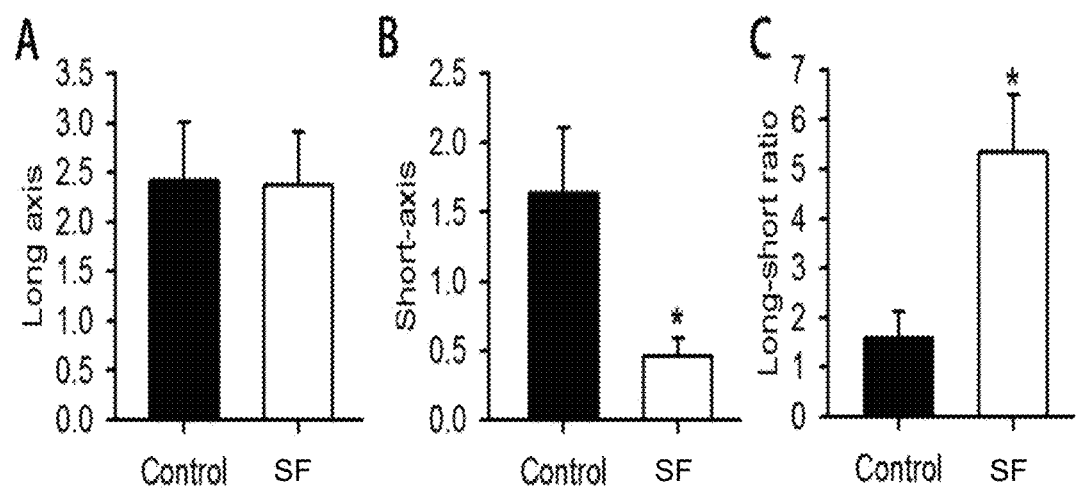
FIG. 8 provides bar graphs illustrating the morphology of cardiomyocytes, according to one working example of the present disclosure.

The dimension of the cells was measured (SF, n=22; control, n=29; 5 independent experiments), in which the longest cell length was considered as the long axis, while the axis perpendicular to the long axis was the short axis. Reference is first made to panel A of FIG. 8, which demonstrated that the lengths of the long axis in both control cells and SF-treated cells were substantially the same (P=0.78). The lengths of the short axis in the aforementioned two groups, however, were statistically different, in which the length of short axis in SF-treated cardiomyocytes was about one-third of that in control cells (panel B, FIG. 8; P<0.001). Hence, the long-to-short axis ratio of the SF-treated cardiomyocytes was significantly greater than that of control cells (panel C, FIG. 8; P<0.001).

These data suggested that the present SF treatment was able to induce the morphological conversion for NRVMs, and the morphology of thus-transformed SAN-like cells bore a high resemblance to native SAN cells.

Example 7

SF-Induced Automaticity in Cardiomyocytes Responds to Autonomic Regulations

Figure 9:
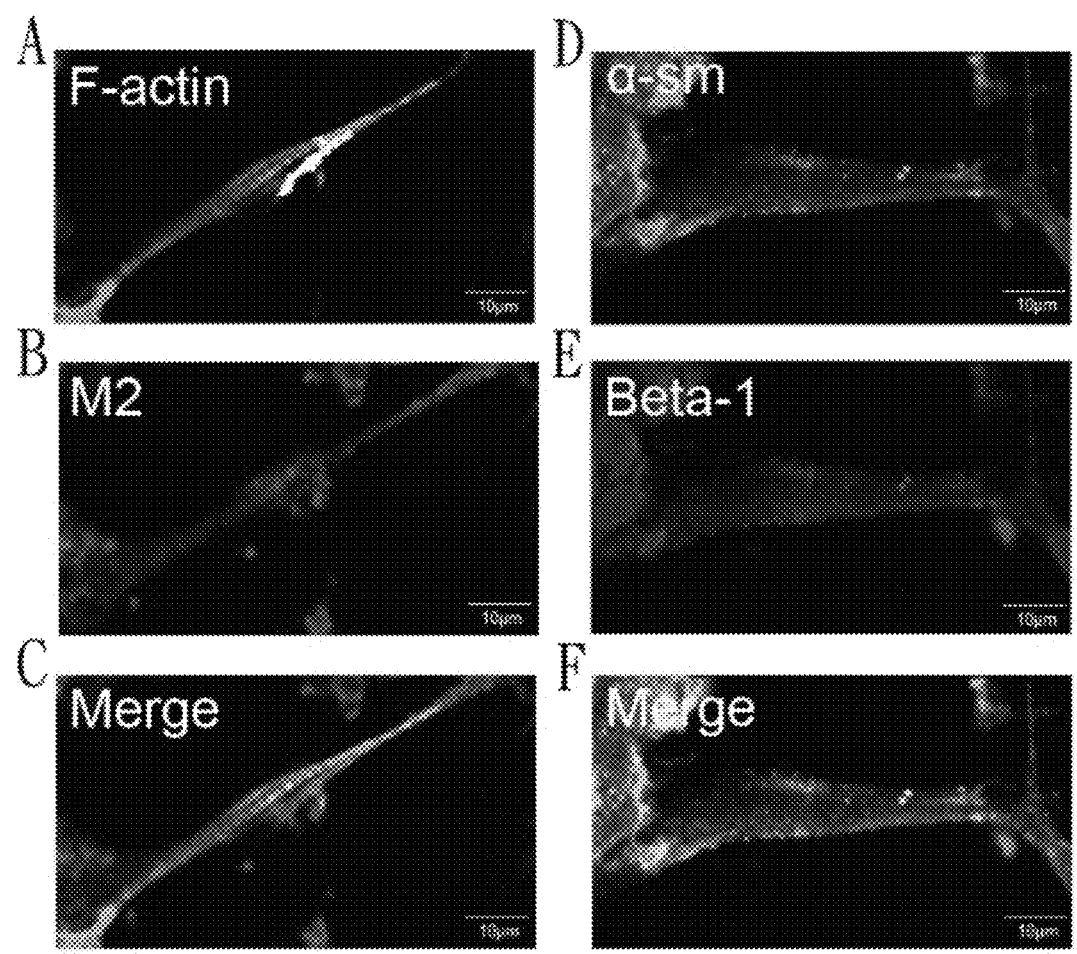
FIG. 9 presents immunostaining images of cardiomyocytes, according to one working example of the present disclosure.

Data form immunostaining analysis demonstrated that muscarinic receptors (M2) and sympathetic receptors (ß1) were expressed in SF-treated cardiomyocytes from Example 1 (see, FIG. 9). In all panels, nuclei were stained with DAPI (blue fluorescence); panel A, green fluorescence: F-actin (a marker for cardiomyocytes); panel B, red fluorescence: muscarinic receptor; panel C: merge image of panels A and B; panel D: green fluorescence: sarcomeric actinin (α-sm, a marker for cardiomyocytes); panel E: red fluorescence: sympathetic ß1 receptor; panel F: merge image of panels D and E.

Figure 10:
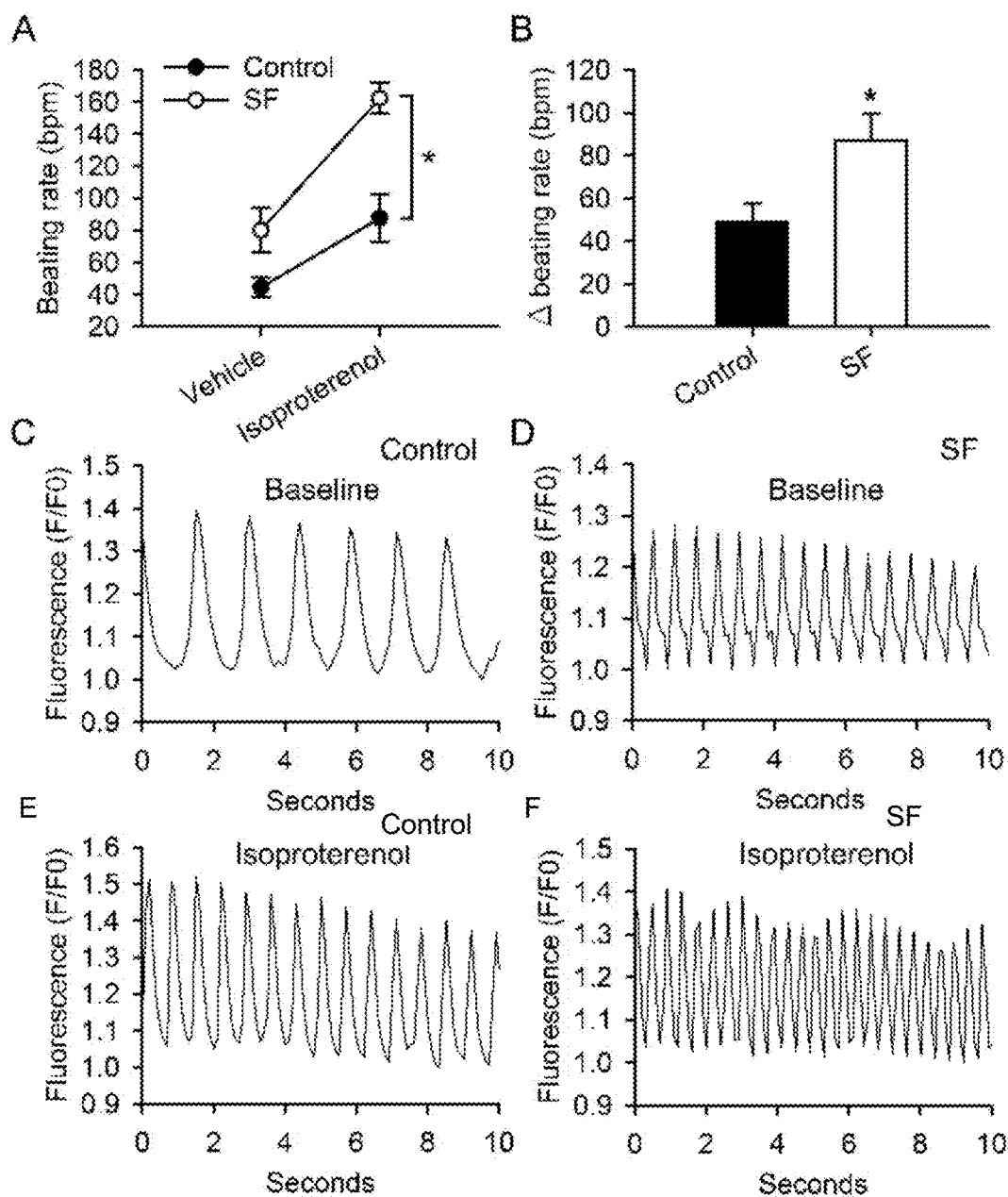
FIG. 10 presents diagrams illustrating the electrophysiology properties of cardiomyocytes, according to one working example of the present disclosure.

Isoproterenol is a non-selective β-adrenergic receptor agonist, which is used for pharmacological sympathetic stimulation to evaluate the physiological sympathetic regulation of sinus node. In this example, the functional regulations of autonomic neurotransmitters in SF-treated cardiomyocytes were investigated using the isoproterenol treatment (1 μM). The results in panel A of FIG. 10 indicated that the treatment of isoproterenol accelerated the beating rate of SF-treated cardiomyocytes to 162.4±9.6 bpm, which was faster than the beating rate of control cells treated isoproterenol (87.6±14.7 bpm), and the differences are regarded as statistical significant (n=10, P=0.001, 5 independent experiments). Moreover, as could be seen in panel B of FIG. 10, an increment of 87.1±12.4 bpm was observed between the beating rates of SF-treated cells without or with the isoproterenol treatment. The increment in SF-treated cardiomyocytes was statistically higher than those (i.e., 49.2±8.3 bpm) between control cells without and with the isoproterenol treatment (n=10, P=0.02, 5 independent experiments). Panels C to E illustrated the calcium transient tracings of cardiomyocytes in control (C, E) and SF-treated (D, F) groups without (C, D) or with (E, F) the isoproterenol treatment; the data in these diagrams indicated that the interval change of beating rate in SF-treated cardiomyocytes was much higher than that of the control cardiomyocytes.

Overall, these data suggested that the beating rate and interval change of beating rate of SF-treated cardiomyocytes were regulated by sympathetic stimulation.

Example 8

SF Induces In Situ Transformation of Cardiomyocytes into Pacemaker Cells 30 to 50 μL of SF hydrogel or saline (control) were injected into the left ventricular apex of rat (male, 10 to 12 weeks old) under thoracotomy. Three weeks later, we ablated the atrioventricular (AV) node and created an AV block under thoracotomy and general anesthesia. Diagrams in FIG. 11A are representative ECG tracing before AV node ablation (baseline) and after AV node ablation in SF-treated (A and B) and control rats (C and D).

Figure 11A:
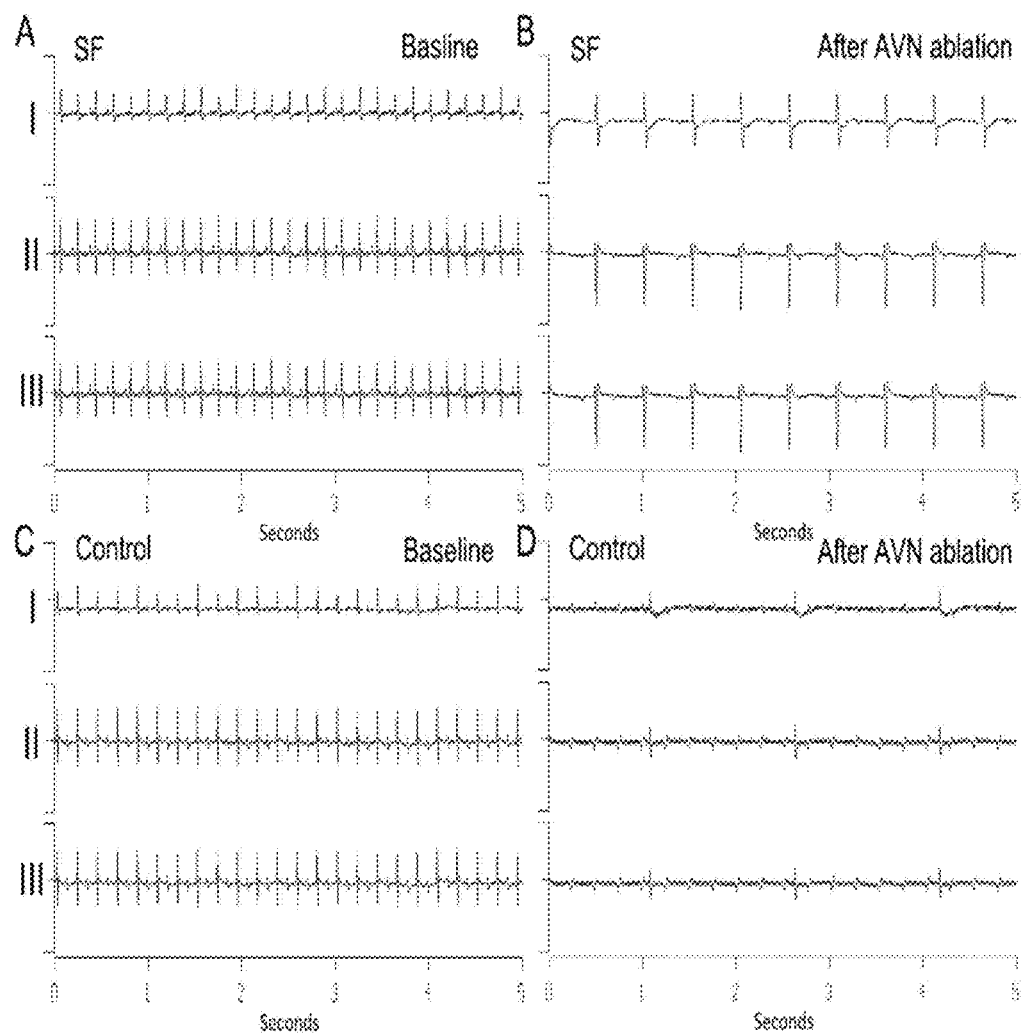
FIG. 11A presents representative diagrams illustrating the electrocardiogram (ECG) tracings of rats before and after AVN ablation (control and treated with 2% (w/w) SF hydrogel)

As could be appreciated, after AV node ablation, the electrical conduction from sinus node was blocked, the escaped junctional rhythm just below the AV node took over the ventricular activation; nonetheless, the rate was very slow (24 bpm) in control rats (FIG. 11A, panel D, lead I). In control rats, the electrical axis remains similar to those conducted from the native AV node—His system; therefore, QRS morphology of lead I, II, and III is all positive (inferior axis), and no electrical firing was noted over the injection site of the LV apex. On the other hand, for rats receiving the SF hydrogel injection, the escaped rhythm came from the LV apex, the injection site (superior axis, negative QRS voltage over lead II and III, with RBBB pattern) at the rate of 120 bpm, and therefore, the axis of electrical conduction was reversed, as compared with that from the native AVN—His system.

Figure 11B:
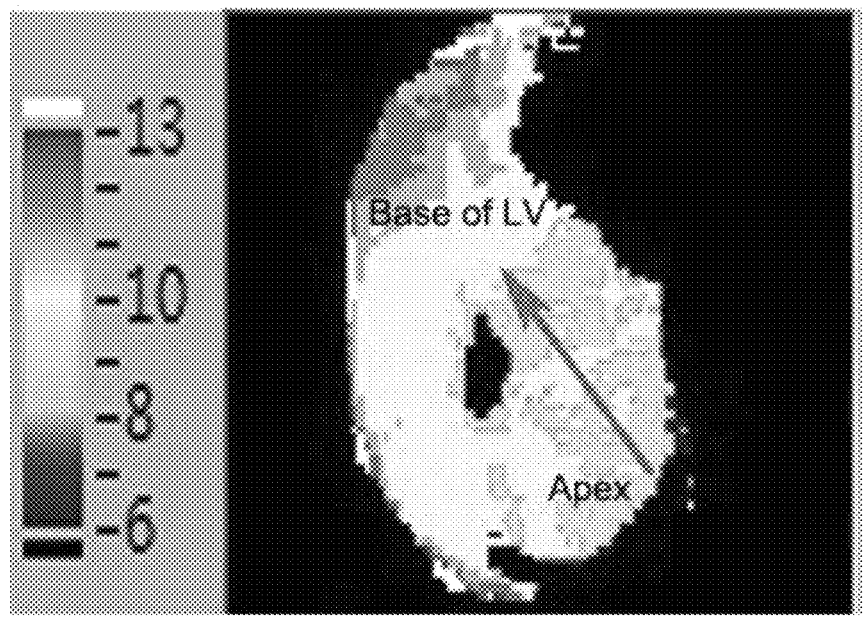
FIG. 11B is an optical mapping of the heart of a representative rate after AVN ablation, according to one working example of the present disclosure.

We further performed optical mapping to determine whether the escape rhythm in SF-treated rat came from the injected site. FIG. 11B is an isochrone map illustrating the activation time in left ventricle; as could be observed in FIG. 11B, the earliest activation site (i.e., the origin of the escape rhythm) came from the injection site of the SF hydrogel, which located at the left ventricular apex.

Figure 11C:
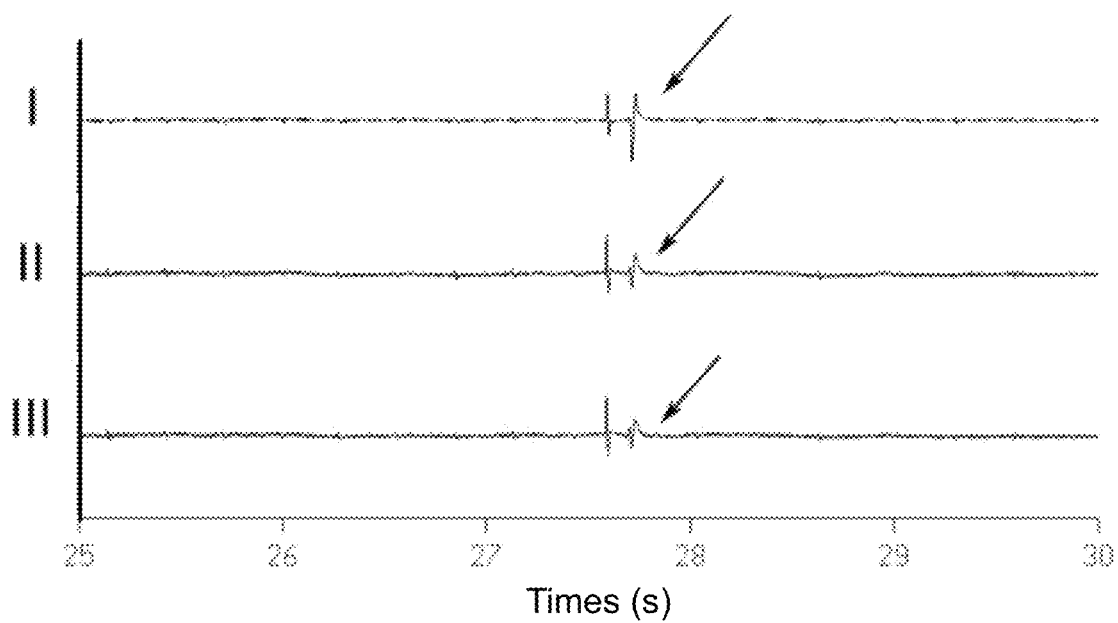
FIG. 11C presents representative diagrams illustrating the ECG tracing of rats after AVN ablation (treated with 12% (w/w) SF solution), according to one working example of the present disclosure.

A concentrated SF solution containing approximately 12% (w/w) silk fibroin was also injected to the left ventricular apex of rats. The results, as provided in FIG. 11C indicated that the injection of the SF solution also induced the in-situ transformation of non-pacemaker cardiomyocytes into pacemaker cells, as several escape rhythms were observed.

Together, these findings indicated that the present SF treatment may induce the formation of pacemaker cells in situ, and these induced peacemaker cell may function as the biological pacemakers to treat bradyarrhythmias when the sinus node or cardiac conduction system is broken.

Example 9

SF-Treated Cardiomyocytes Express Pacemaker-Specific Transcriptional Factors

Figure 12:
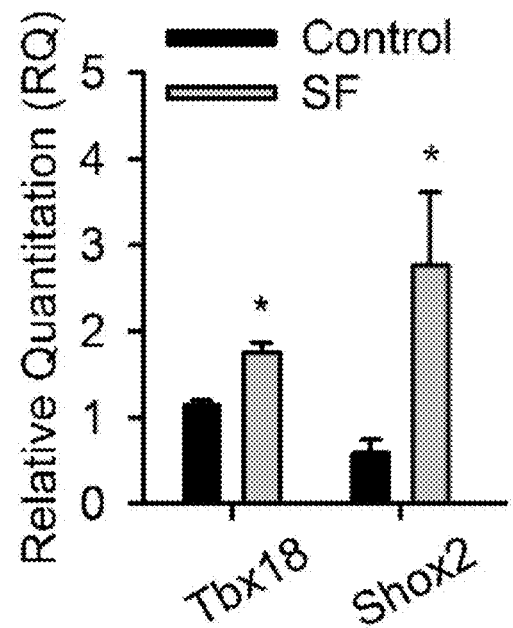
FIG. 12 is a bar graphs illustrating the relative quantitation of different marker genes in cardiomyocytes, according to one working example of the present disclosure.

Recent research revealed that during the embryogenesis stage, the simultaneous activation of Tbx18 and Shox2 plays an important role in the differentiation of SAN progenitors to mature SAN cells. In this example, the expressions of these transcriptional factors in SF-treated cardiomyocytes from Example 1 were determined. The results, as summarized in FIG. 12, indicated that the expressions of both transcriptional factors were increased significantly in SF-treated cardiomyocytes, as compared with those in control cells (n=7-10, P<0.05).

The upregulation of transcriptional factors such as Tbx18 and Shox2 observed herein is in line with the expression profile of SAN cells in the embryogenesis phase.

Example 10

SF-Treated Cardiomyocytes Exhibit Comparable Beating Rate in Relative to TBX18-Reprogrammed Cardiomyocytes Adenoviral TBX18 vector (Vector Biolabs (Philadelphia, PA, USA); Human TBX18, BC157841) transduction has been used to create biological pacemaker in several animal models, including Guinea pigs and pigs. The adenoviral TBX18 gene therapy has been moving into a phase I clinical study.

Figure 13:
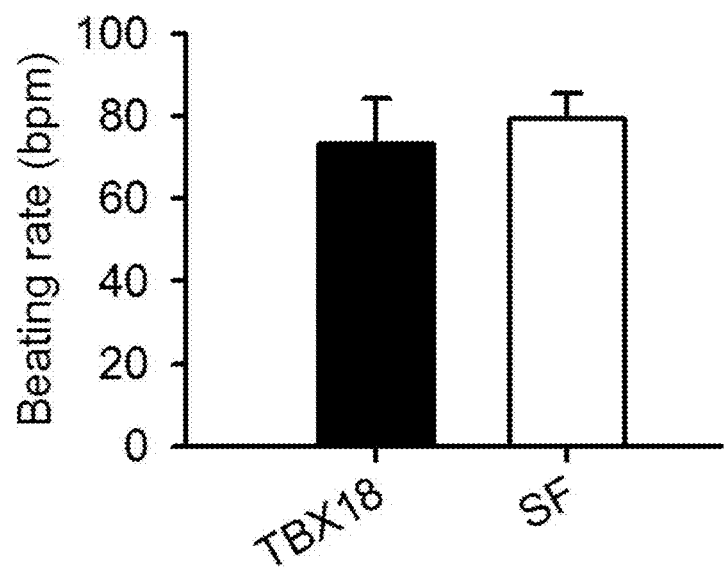
FIG. 13 is a bar graphs illustrating the beating rate in cardiomyocytes, according to one working example of the present disclosure.

The data in FIG. 13 demonstrated that there was no statistically significant difference between the maximal beating rates observed in SF-treated cardiomyocytes and neonatal cardiomyocytes 3 days after the treatment of TBX18 adenoviral vectors (SF, n=50; TBX18, n=9; P=0.69). Since the maximal beating rates of SF-treated cardiomyocytes and TBX18-reprogrammed cardiomyocytes were comparable, it is believed that the present SF-treated cardiomyocytes have a great potential for clinical application as the biological pacemaker.

The experimental data provided in the present disclosure established that non-pacemaker cardiomyocytes could be effectively transformed into cells with pacemaker activity by the treatment of silk fibroin. The transformed cells have distinct electrophysiologic characteristics, as well as morphology characteristics, that are not seen in their non-transformed counterparts. Moreover, the gene expression profile of transformed cells is similar to that of native sinoatrial node pacemaker cells, and they undergo similar regulatory mechanisms as the natural pacemaker cells do. Taken together, the transformed cardiomyocytes are comparable to natural sinoatrial node pacemaker cells in terms of their function, morphology, gene expressions, and regulatory mechanisms. Accordingly, the silk fibroin-transformed cardiomyocytes are SAN-like cells and may be used to take place of the natural pacemaker cell in the patients with sinoatrial node damage or other condition associated with cardiac arrhythmias.

It will be understood that the above description of working examples and embodiments is given by way of example only, and that various modifications may be made by those with ordinary skill in the art. The above specification, examples and data provide a complete description of the structure and use of exemplary embodiments of the invention. Although various embodiments of the invention have been described above with a certain degree of particularity or with reference to one or more individual embodiments, those with ordinary skill in the art could make numerous alterations to the disclosed embodiments without departing from the spirit or scope of this invention.

What is claimed is:

1. A method of treating a subject suffering from cardiac arrhythmia, consisting of the step of administering to the heart of the subject an effective amount of a silk fibroin of *Bombyx mori*.

2. The method of claim 1, wherein the silk fibroin of *Bombyx mori* is in the form of a silk fibroin solution, a silk fibroin particle, a non-woven silk fibroin mat, a silk fibroin hydrogel, a silk fibroin film, or a silk fibroin scaffold.

3. The method of claim 2, wherein the silk fibroin film comprises a biodegradable polymeric film having a plurality of amine groups on the surface thereof, and a plurality of silk fibroins crosslinked with the biodegradable polymeric film via the plurality of amine groups.

\* \* \* \* \*